United States Patent [19]

Leibowitz

[11] Patent Number: 4,806,347

[45] Date of Patent: Feb. 21, 1989

[54] INTERFERON COMBINATIONS

[75] Inventor: Paul J. Leibowitz, Hackensack, N.J.

[73] Assignee: Schering Corporation, Kenilworth, N.J.

[21] Appl. No.: 807,887

[22] Filed: Dec. 11, 1985

[51] Int. Cl.$^4$ .................................................. A61K 45/02
[52] U.S. Cl. .................................... 424/85.5; 435/811; 424/85.4
[58] Field of Search ...................... 424/85; 435/68, 811

[56] References Cited

U.S. PATENT DOCUMENTS

| 4,414,150 | 11/1983 | Goeddel | 435/68 |
| 4,456,748 | 6/1984 | Goeddel | 435/68 |
| 4,678,751 | 7/1987 | Goeddel | 435/243 |

FOREIGN PATENT DOCUMENTS

| 051873 | 6/1982 | European Pat. Off. . |
| 0107498 | 5/1984 | European Pat. Off. . |
| 0146903 | 7/1985 | European Pat. Off. . |

OTHER PUBLICATIONS

Rehberg et al., J. Biol. Chem., vol. 257, pp. 11497–11503, 1982.
Weck, et al., Nucleic Acid Research, vol. pp. 6153–6166, 1981.
Petka et al., Methods In Enzymology, vol. 78, pp. 3–6, Academic Press, New York, 1981.

Primary Examiner—Blondel Hazel
Attorney, Agent, or Firm—Gerald S. Rosen; Thomas D. Hoffman; Stephen I. Miller

[57] ABSTRACT

There are disclosed compositions and methods for treating tumors and viruses in humans by administering a combination of gamma interferon and delta-4 alpha-2 (Bgl II-1)/(Bgl II) alpha-1 hybrid interferon, preferably by injection.

10 Claims, No Drawings

INTERFERON COMBINATIONS

BACKGROUND

This invention relates to combinations of (a) human gamma interferon (IFN-γ), sometimes referred to as human immune interferon, with (b) synthetic abbreviated leukocyte interferon (IFN-α), which features a "sub-segment" defined as delta-4- alpha-2 (Bgl II-1) derived from an alpha-2 sequence that is joined to a segment defined as (Bgl II) alpha-1 derived from an alpha-1 sequence, which combinations display greater antiproliferative effects against human tumor cells and greater antiviral activity than could be expected from their individual activities.

There are a number of interferon hybrid made by recombinant techniques wherein two or more leukocyte interferon segments are combined by use of now standard recombinant DNA methods. Such hybrid are disclosed in U.S. Pat. Nos. 4,456,748 and 4,414,150 as well as in European Patent Application Publication No. 0051873, (May 19, 1982) and Weck et al., Nucleic Acids Research 9, 6153, (1981). However, there is no disclosure of a delta-4 α-interferon, i.e. one missing the first 4-amino acids.

European Patent Application Publication No. 0107498, (Oct. 24, 1983) discloses combinations of gamma interferon and, inter alia, "hybrid interferons" such as those disclosed in Weck et al and European Patent Application Publ. No. 00518731 as displaying "synergistic" biological activity as evidenced by antiproliferative effects against the human melanoma cell line Hs294T. However, there is no disclosure of a delta-4 hybrid.

European Patent Application Publication No. 0146903, (July 3, 1985) discloses a synthetic abbreviated interferon which exemplifies the preferred interferon hybrid suitable for use in this invention, i.e. delta-4 alpha-2 (Bgl II-1) derived from an alpha-2 sequence that is joined to a segment defined as (Bgl II) alpha-1 derived from an alpha-1 sequence.

SUMMARY OF THE INVENTION

This invention is directed to pharmaceutical compositions comprising human gamma interferon (IFN-γ) in a pharmaceutically pure mixture with the synthetic abbreviated interferon hybrid disclosed in European Patent Applicatin Publication No. 0146903 which is incorporated by reference herein. The synthetic abbreviated interferon hybrid used in this invention is identified in said European Patent Application Publication No. 0146903 as delta-4 alpha-2 (Bgl II-1) derived from an alpha-2 sequence that is joined to a segment defined as (Bgl II) alpha-1 derived from an alpha-1 sequence. It will be referred to as "delta-4 alpha-2 (Bgl II-1)/(Bgl II) alpha-1 hybrid interferon". Methods of treating human tumors with said compositions and methods of treating viruses with said compositions are also included in the invention.

Gamma interferon, both naturally occurring and recombinant, and the delta-4 alpha-2 (Bgl II-1)/(Bgl II) alpha-1 hybrid interferon a synthetic abbreviated interferon hybrid, which is made as disclosed in said European Patent Application Publication No. 0146903, are each known to have anti-tumor activity, i.e. they manifest antiproliferative effects when used to treat tumor cells and they also are known to have antiviral effects. However, their individual effects are such that effective use requires doses as large that toxic side effects occur. There is therefore a need for a means to achieve the same or better antiproliferative effects against tumors or the same or better antiviral effects with lower doses of the interferons used so that the toxic side effects are either eliminated or reduced to a tolerable level.

DETAILED DESCRIPTION

This invention provides compositions and methods for treating susceptible tumors and susceptible viruses utilizing lowr doses of gamma interferon and delta-4 alpha-2 (Bgl II-1)/(Bgl II) alpha-1 hybrid interferon in combination than required if each is used alone.

More particularly, this invention is based on the discovery that a pharmaceutical composition containing an anti tumor effective amount or an antiviral effective amount of a combination of gamma interferon and delta-4 alpha-2 (Bgl II-1)/(Bgl II) alpha-1 hybrid interferon is more effective in treating susceptible tumors or susceptible viruses than would be expected from their individual potencies. In addition this invention provides a method of treating human tumors or viruses by administering to a patient in need of such treatment a pharmaceutical composition comprising an effective amount of a combination of gamma interferon and delta-4 alpha-2 (Bgl II-1)/(Bgl II) alpha-1 hybrid interferon in a pharmaceutically acceptable carrier. The invention also provides a method of treating human tumors or viruses by administering to a patient in need of such treatment a combination of gamma interferon and delta-4 alpha-2 (Bgl II-1)/(Bgl II) alpha-1 hybrid interferon in amounts effective to exhibit antiproliferative or antiviral effects wherein the active ingredients can be administered separately in any effective sequence, or simultaneously.

Administration of the compositions or combinations of this invention can be via any of the accepted modes of administration for anti-tumor or antiviral interferons. These methods include oral, parenteral, topical, depot and transdermal. Subcutaneous or intravenous injection is preferred.

Depending on the intended mode of administration, the compositions containing the gamma and/or delta-4 alpha-2 (Bgl II-1)/(Bgl II) alpha-1 hybrid interferons may be in the form of solid, semi-solid or liquid dosage forms, such as, for example, tablets, pills, capsules, powders for reconstitution, liquids, suspensions, or the like preferably in unit dosage forms suitable for single administration of precise dosages.

The pharmaceutically acceptable carriers and excipients useful in this invention are conventional. There may be included other medicinal and pharmaceutical agents. Excipients which may be included, can be, but are not limited to, other proteins, such as, human serum albumin or plasma preparations.

The amount of active compound administered will, of course, be dependent on the subject being treated, the severity of the affliction and the manner of administration in the judgment of the prescribing physician.

For solid compositions, conventional non-toxic solid carriers include, for example, pharmaceutical grades of mannitol, lactose, starch, or magnesium stearate. Liquid injectable pharmaceutically administerable compositions can, for example, be prepared by dissolving, dispersing, etc. in a carrier, such as, for example, water, saline, aqueous dextrose, glycerol, ethanol, and the like, to thereby form a solution or suspension for injection. If desired, the pharmaceutical composition to be administered may also contain minor amounts of nontoxic auxiliary substances such as wetting or emulsifying agents, preservatives, pH buffering agents and the like, for example, sodium acetate or sorbitan monolaurate. Actual methods of preparing such dosage forms are known, or will be apparent, to those skilled in this art; for example, see *Remingtons's Pharmaceutical Sciences*, Mack Publishing Company, Easton, Pa., 15 Edition, 1975. The composition or formulation to be administered will, in any event, contain a quantity of the active component(s) in an amount effective to achieve the desired effect in the subject being treated.

The combination of gamma interferon and delta-4 alpha-2 (Bgl II-1)/(Bgl II) alpha-1 hybrid interferon can contain a wide range of international reference units per ml (IRU/ml) of each interferon and still display a greater than additive effect against tumors or viruses, for examples, the amount of gamma interferon administered can be from about $0.02 \times 10^6$ IRU/meter square to $2 \times 10^6$ IRU/meter square and the amount of delta-4 alpha-2 (Bgl II-1)/(Bgl II) alpha-1 hybrid interferon administered can be from about $0.02 \times 10^6$ IRU/meter square to $10 \times 10^6$ IRU/meter square.

The combination of interferons used according to this invention should exhibit greater than additive effects against viruses such as the polio-like virus EMC and the rabies-like virus VSV.

The following illustrates the antiproliferative effects of combining gamma interferon with an abbreviated interferon hybrid containing a delta-4 alpha-2 (Bgl II-1)/(Bgl II) alpha-1 component.

MATERIALS AND METHODS

Cell Lines.

The human bladder carcinoma cell line RT4, Rigby et al, British J Cancer 24, 746 (1970), and the human lung carcinoma cell line A2182 (S. A. Aaronson, National Cancer Institute) were maintained in RPMI 1640 medium supplemented with 10% heat inactivated fetal calf serum 2 mM glutamine penicillin and streptomycin (complete medium) at 37° C. in a humidified $CO_2$ atmosphere. The cells were subcultured with a 0.25% trypsin (Worthington)—EDTA solution when the cells were approximately 80% confluent.

Interferons.

A delta-4 containing hybrid interferon which contains amino acids 5-62 of alpha-2 IFN and 64-166 of alpha-1 IFN (specific activity $1.0 \times 10^8$ IRU/mg) was diluted with phosphate buffered saline, pH 7.4, containing 3.5 mg/ml human serum albumin, aliquoted and stored at $-70°$ C. until use. Its specific activity was calculated using NIH natural $\alpha$-IFN WHO/NIH 69/19 (specific activity $3 \times 10^6$ IRU/mg) as a standard. Recombinant gamma interferon (specific activity $4.0 \times 10^6$ IRU/mg) was stored undiluted at 4° C. until use. The specific activity of the recombinant gamma IFN was calculated using NIH natural $\gamma$-IFN Gg23-901-530 (specific activity $7 \times 10^5$ IRU/mg) as a standard.

Antiproliferative Assays.

Assays of cell growth inhibition were performed as previously described, Hubbell et al. Cancer Res 44, 3252 (1984),. Cells in log phase growth were used for the assay. On day $-1$, $1 \times 10^5$ cells were plated on 35 mm Petri dishes and allowed to attach overnight. At time 0, the medium was aspirated, the plates washed once with Hanks' balanced salt solution (HBSS) and then refed with fresh medium alone or containing the appropriate concentration of interferon (IFN). For experiments with the combination of this invention the cells were fed with fresh medium containing a mixture of the IFNs at the appropriate concentration. After a 72 hr incubation period, the cells were counted in a Coulter counter, model $Z_{BI}$, as follows. The cells were washed once with HBSS, removed from the plates with trypsin and added to an equal volume of complete medium. The plates were rinsed once with complete medium which was combined with the cell suspension. The cells were diluted 10-fold with TBS (20 mM Tris, pH 7.5, 150 mM NaCl) for counting. The % control growth was calculated from the formula:

$$\frac{\text{Treated cells day 3} - \text{Control cells day 0}}{\text{Control cells day 3} - \text{Control cells day 0}} \times 100$$

Statistical Analysis.

Results were analyzed by linear regression analysis using the logarithm of the IFN concentration vs. the calculated % control growth. The statistical validity of each experiment was verified by the correlation coefficient (r) for each regression line. All r values were greater than 0.78. The amount of IFN needed to inhibit growth by 50% ($GI_{50}$) was derived from the regression analysis and used as a point of comparison, Hubbell et. al., supra. Significance (p) values were calculated for the comparison of effectiveness of the INFs used individually by three way analysis of variance and Scheffe's multiple contrast method, Zar, Biostatistical Analysis, Prentice Hall. Inc. 105-107, 159-161, 190-193 (1974).

The extent of the effect of the combined IFN treatments were calculated by the isobole method for a combination for drugs A and B, Berenbaum, Advances in Cancer Research, 25 269 (1981), from the equation $$\frac{A_c}{A_e} + \frac{B_c}{B_e} = D$$

where $A_c$ and $B_c$ are the doses of the drugs used in the combination treatment and $A_e$ and $B_e$ are the doses of the drugs used individually to give the same magnitude of effect as in the combination. If $D<1$ the IFN combination gives more than an additive antiproliferative effect. If $D=1$ the effect is additive and if $D<1$ the effect is antagonistic. The values for $A_e$ and $B_e$ were derived from a line generated by the dose-response curves obtained for each IFN individually on each cell line by using the average slope of multiple experiments. The y-intercept was determined by using the value of each IFN alone obtained in the experiments. Interferon potentiation was calculated as the amount of the delta-4 alpha-2 (Bgl II-1)/(Bgl II) alpha-1 hybrid interferon used alone to give the same effect as the combination with gamma interferon ($A_e$) divided by the amount of the delta-4 alpha-2 (Bgl II-1)/(Bgl II) alpha-1 hybrid IFN used in the combination ($A_c$). Duplicate or triplicate experiments allowed a calculation of the statistical significance values (p) of the combination indices (D) compared to the additive combination index of $D=1$ by the one-sided Student's t test, Zar, supra.

RESULTS

The results are shown in the Tables which follow.

Antiproliferative Effect of IFNs.

RT4 and A2182 cells were treated in a dose-response manner, range 100-5000 IRU/ml for delta-4 alpha-2 (Bgl II-1)/(Bgl II) alpha-1 hybrid IFN, 10-500 IRU/ml for gamma IFN. RT4 cells were overall more sensitive to the antiproliferative effects of the IFNs than A2182 cells.

TABLE 1

Relative Effectiveness of delta-4 alpha-2 (Bgl II-1)/(Bgl II) alpha-1 hybrid and Gamma Interferons as Antiproliferative Agents

| Cell Line | Interferon | $GI_{50}$[a] IRU/ml[b] |
|---|---|---|
| RT4 | delta-4 alpha-2 (Bgl II-1)/(Bgl II) alpha-1 hybrid | 1050 |
|  | Gamma | 14[c] |
| A2182 | delta-4 alpha-2 (Bgl II-1)/(Bgl II) alpha-1 hybrid | 4700 |
|  | Gamma | 390[c] |

[a]All values average of two experiments, unless otherwise noted.
[b]International reference units per milliliter.
[c]Average of three experiments.

Table 1 summarizes the dose-response results by comparing the $GI_{50}$ values for gamma and delta-4 alpha-2 (Bgl II-1)/(Bgl II) alpha-1 hybrid subsegment IFNs. On an IRU/ml basis, the gamma IFN is significantly more effective than the delta-4 alpha-2 (Bgl II-1)/(Bgl II) alpha-1 hybrid IFN in both RT4 and A2182 cells.

Antiproliferative Effect of IFN Combinations.

All cell lines were treated with combinations of the gamma and the delta-4 alpha-2 (Bgl II-1)/(Bgl II) alpha-1 hybrid IFN preparations to assess the potential for potentiated antiproliferative effects. In these experiments, doses of the IFNs were used which alone caused only limited inhibition of tumor cell growth. The potentiation in each experiment was calculated using a line generated from the individual treatments of the experiments and the average slope from independently generated dose-response curves.

TABLE 2

Potentiated Antiproliferative Combinations of delta-4 alpha-2 (Bgl II-1)/(Bgl II) alpha-1 hybrid Interferon and Gamma Interferon in the Bladder Carcinoma cell Line RT 4

| $IFN(A_c)$ IRU/ml | Gamma $IFN(B_c)$ IRU/ml | % Control Growth | $IFN(A_e)$ IRU/ml | Gamma $IFN(B_e)$ IRU/ml | Combination Index(D) |
|---|---|---|---|---|---|
| Experiment I Delta-4 100 | 5.0 | 13.6 | >5,000 | 50 | <0.120 |
| Experiment II Delta-4 100 | 5.0 | −34.1 | >5,000 | >500 | <0.030 |
| Experiment III Delta-4 100 | 5.0 | −12.0 | >5,000 | >500 | <0.030 |

Table 2 summarizes the results of three experiments on RT4 cells using gamma IFN in combination with each of the delta-4 alpha-2 (Bgl II-1)/(Bgl II) alpha-1 hybrid IFN preparations. Statistical analysis of the experimental combination index (D) values compared to D=1 (additive effect) indicates that gamma IFN in combination with the delta-4 alpha-2 (Bgl II-1)/(Bgl II) alpha-1 hybrid IFN studies inhibited tumor cell growth in a more than additive manner (p<0.05). For each combination, 100 IRU/ml of the delta-4 alpha-2 (Bgl II-1)/(Bgl II) alpha-1 hybrid IFN was used, however, the amount alone necessary to be as effective as the combination was greater than 5000 IRU/ml. Thus, in all cases, the gamma IFN potentiated the delta-4 alpha-2 (Bgl II-1)/(Bgl II) alpha-1 hybrid effect greater than 50-fold.

TABLE 3

Potentiated Antiproliferative Combinations of delta-4 alpha-2 (Bgl II-1)/(Bgl II) alpha-1 hybrid Interferon and Gamma Interferon in the Lung Carcinoma Cell Line A2182

| IFN(A) IRU/ml | Gamma $IFN(B_c)$ IRU/ml | % Control Growth | $IFN(A_e)$ IRU/ml | Gamma $IFN(B_e)$ IRU/ml | Combination Index |
|---|---|---|---|---|---|
| Experiment I Delta-4 100 | 20 | 13.1 | >5,000 | 178 | <0.132 |
| Experiment II Delta-4 100 | 20 | 21.6 | >5,000 | >500 | <0.060 |
| Experiment III Delta-4 100 | 20 | 22.2 | >5,000 | 302 | <0.086 |

The data in Table 3 show that gamma interferon in combination with delta-4 alpha-2 (Bgl II-1)/(Bgl II) alpha-1 hybrid interferon exhibits greater than additive effects in A2182 cells. Statistical analysis indicates that all gamma interferon/delta-4 alpha-2 (Bgl II-1)/(Bgl II) alpha-1 hybrid interferon combinations inhibit A2182 cell growth in a more than additive manner (p<0.05). The gamma interferon potentiates the delta-4 alpha-2 (Bgl II-1)/(Bgl II) alpha-1 hybrid interferon greater than 50-fold.

Gamma Interferon Concentration and Magnitude of Potentiations.

In order to determine the contribution of gamma interferon to the potentiated antiproleferative effects seen in the delta-4 alpha-2 (Bgl II-1)/(Bgl II) alpha-1 hybrid IFN/gamma IFN combinations, the amount of gamma IFN was varied over a 10-fold range in RT4 cells.

TABLE 4

Variation in Potentiated Antiproliferative Effect with Different Gamma Interferon concentrations in RT4 Cells

| $IFN(A_c)$ IRU/ml Delta-4 | Gamma $IFN(B_c)$ IRU/ml | % Control Growth | $IFN(A_e)$ IRU/ml | Gamma $IFN(B_e)$ IRU/ml | Combination Index(D) |
|---|---|---|---|---|---|
| 100 | 0.2 | 124.4 | 162 | 0.03 | 8.61 |
| 100 | 0.5 | 113.0 | 417 | 0.22 | 2.51 |
| 100 | 2.0 | 56.1 | >5,000 | 7.59 | <0.28 |
| 100 | 5.0 | 17.0 | >5,000 | 79.00 | <0.08 |

As seen in Table 4, the concentration of gamma IFN plays a significant role in the magnitude of potentiation obtained. Gamma IFN at 0.2 and 0.5 IRU/ml, in combination with the delta-4 alpha-2 (Bgl II-1)/(Bgl II) alpha-1 hybrid IFN, shows a slight stimulation of cell growth and a clear cut antagonistic effect is seen at the lower gamma IFN concentrations. The effectiveness of the arious gamma IFN concentrations is also related to the potency of the delta-4 alpha-2 (Bgl II-1)/(Bgl II) alpha-1 hybrid IFN used in the combination. Potentiation is seen at 2.0 and 5.0 IRU/ml gamma IFN with the delta-4 alpha-2 (Bgl II-1)/(Bgl II) alpha-1 hybrid IFN.

DISCUSSION

The two cell lines studies here were inhibited in a dose-dependent manner by the various IFN preparations. In general, RT4 cells were more sensitive to delta-4 alpha-2 (Bgl II-1)/(Bgl II) alpha-1 hybrid IFN than A2182 cells. When calculated on an IRU/ml basis, gamma IFN was more effective in both cell lines.

As the data in the Tables indicate, combinations of gamma IFN with the delta-4 alpha-2 (Bgl II-1)/(Bgl II) alpha-1 hybrid IFN yielded more than additive antitumor effects in both cell lines. The antigrowth effects of the delta-4 alpha-2 (Bgl II-1)/(Bgl II) alpha-1 hybrid IFN were potentiated greater than 50-fold by the gamma IFN. Significant greater than additive antitumor effects were seen in the A2182 cells, even though these cells were relatively resistant to delta-4 alpha-2 (Bgl II-1)/(Bgl II) alpha-1 hybrid IFN alone. Variation of the gamma IFN in RT4 cells demonstrated that potentiation occurred within a particular range of IFN concentrations. The potency of the delta-4 alpha-2 (Bgl II-1)/(Bgl II) alpha-1 hybrid IFN also appeared to determine at what concentrations gamma IFN would potentiate. A relatively low concentration was used for all delta-4 alpha-2 (Bgl II-1)/(Bgl II) alpha-1 hybrid IFN preparations (100 IRU/ml) and potentiation was seen at a lower concentration of gamma IFN (2.0 IRU/ml) using the most potent delta-4 alpha-2 (Bgl II-1)/(Bgl II) alpha-1 hybrid IFN preparation. In the experiments used in this application highly purified recombinant IFN preparations were used.

The results indicate that the clinical use of delta-4 alpha-2 (Bgl II-1)/(Bgl II) alpha-1 hybrid/gamma IFN combinations may be more successful than present single IFN therapies. Significant decreases in the needed dose of the IFNs has the advantage of minimizing toxic side effects during treatment. In addition, the range of patients responding to therapy should be significantly increased. These results indicate that combination therapy, in general, should greatly increase the range of sensitive tumors and, specifically, that delta-4 alpha-2 (Bgl II-1)/(Bgl II) alpha-1 hybrid/gamma IFN therapy may be effective in tumors presently resistant to these different biological response modifiers and display antiproliferative effects where before either delta-4 alpha-2 (Bgl II-1)/(Bgl II) alpha-1 hybrid or gamma interferons were separately ineffective.

I claim:

1. A pharmaceutical composition comprising a combination of gamma interferon in a pharmaceutically pure mixture with a second interferon which is delta-4 alpha-2 (Bgl-II-1/Bgl-II) alpha-1 hybrid interferon and a pharmaceutically acceptable carrier.

2. A composition of claim 1 which is an injectible composition.

3. A pharmaceutical composition of claim 1 which comprises an anti-tumor effective amount of said combination.

4. A pharmaceutical composition of claim 1 which comprises an antiviral effective amount of said combination.

5. A method of treating susceptible tumors which comprises administering to a patient in need of such treatment, an antiproliferative effective amount of the composition of claim 1.

6. A method of treating susceptible tumors which comprises administering to a patient in need of such treatment, an antiproliferative effective amount of a combination of gamma interferon and delta-4 alpha-2 (Bgl II-1)/(Bgl II) alpha-1 hybrid interferon.

7. A method of claim 5 in which the administration is by injection.

8. A method of claim 6 in which the administration is by injection.

9. A method of treating susceptible viruses which comprises administering to a patient in need of said treatment, an antiviral effective amount of a combination of gamma interferon and delta-4 alpha-2 (Bgl II-1)/(Bgl II) alpha-1 hybrid interferon.

10. A method of claim 9 in which the administration is by injection.

* * * * *